United States Patent [19]
Schlatter et al.

[11] 3,952,592
[45] Apr. 27, 1976

[54] FLUID SENSING SYSTEMS

[75] Inventors: Gerald Lance Schlatter; Charles Eveleigh Miller, both of Boulder, Colo.

[73] Assignee: International Telephone and Telegraph Corporation, New York, N.Y.

[22] Filed: Nov. 24, 1972

[21] Appl. No.: 309,250

Related U.S. Application Data
[62] Division of Ser. No. 187,948, Oct. 12, 1971.

[52] U.S. Cl. ............................ 73/194 R; 73/231 R
[51] Int. Cl.² ...................................... G01F 1/115
[58] Field of Search .......... 73/194 E, 194 R, 231 R, 73/453; 235/151.34, 92 MT, 92 FL

[56] References Cited
UNITED STATES PATENTS

| | | | |
|---|---|---|---|
| 2,803,960 | 8/1957 | Hart | 73/453 X |
| 2,992,561 | 7/1961 | Burt | 73/453 |
| 3,040,585 | 6/1962 | Chatel et al. | 73/453 |
| 3,154,950 | 11/1964 | Hargens et al. | 73/453 |
| 3,385,108 | 5/1968 | Rosso | 73/194 R |

Primary Examiner—James J. Gill
Attorney, Agent, or Firm—A. Donald Stolzy

[57] ABSTRACT

A net oil computer including a vibration densitometer and a turbine flowmeter. The flowmeter produces output pulses at a frequency directly proportional to the rate of volume flow through a pipeline. The output of the flowmeter is impressed upon the pole of a single pole, double throw electronic switch. One switch contact is connected to an indicator through a divider, a driver amplifier and a counter. The other contact is also connected to an indicator through a divider, a driver amplifier and a counter. The switch is operated by a gate generator connected from the densitometer. The gate generator produces an output pulse of a pulse width directly proportional to the percent of oil or water in the pipeline. A temperature probe is inserted in the line to vary the pulse width in accordance with oil temperature. The densitometer has an improved magnetostrictive drive which is controlled to have a phase proper for maximum resonance. The densitometer is also provided with a self-start circuit to find resonance automatically. A synchronous detector detects resonance and automatically turns the self-start circuit off.

13 Claims, 23 Drawing Figures

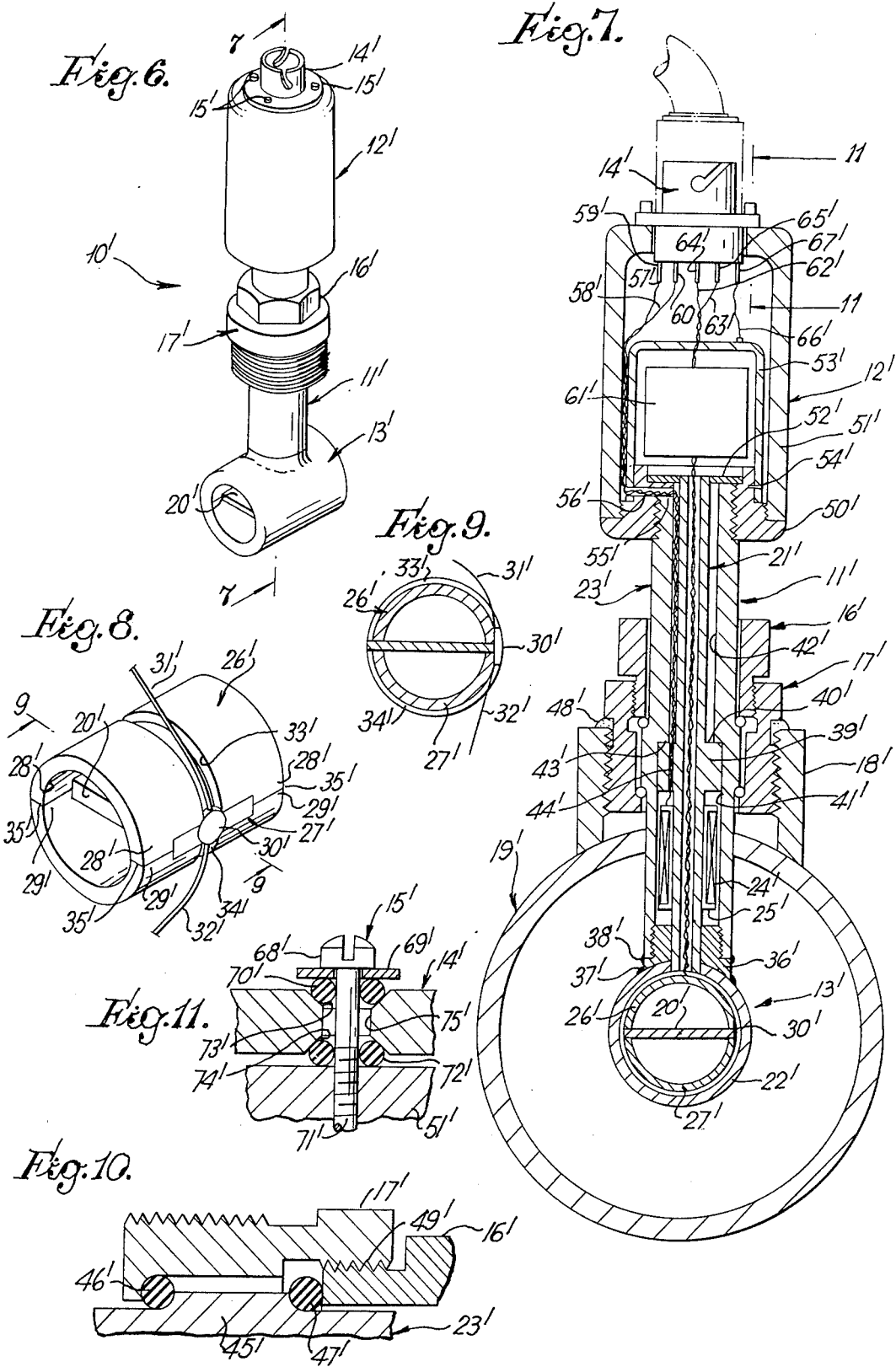

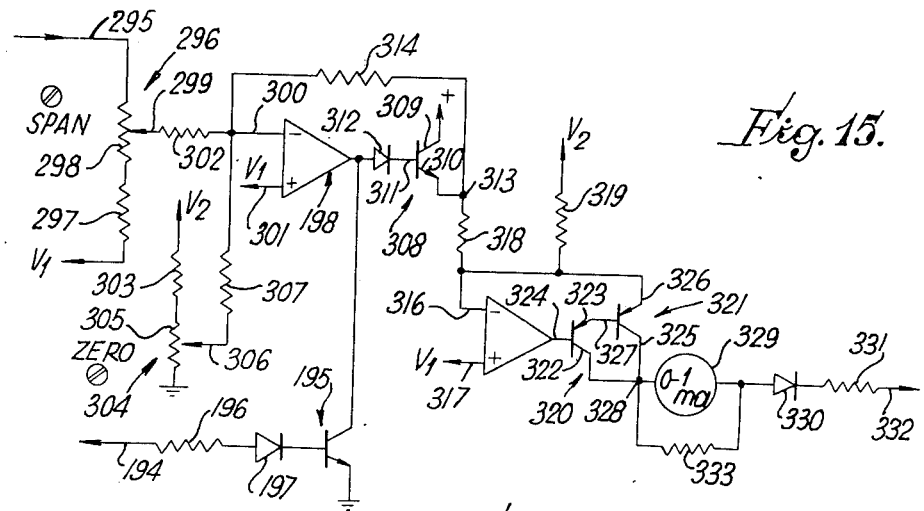
Fig. 15.
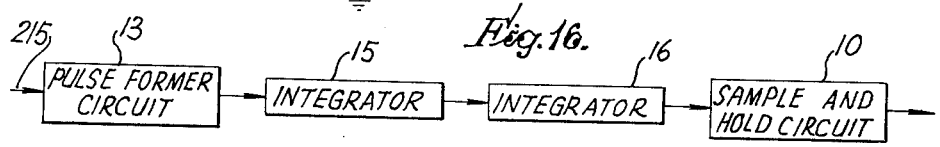
Fig. 16.
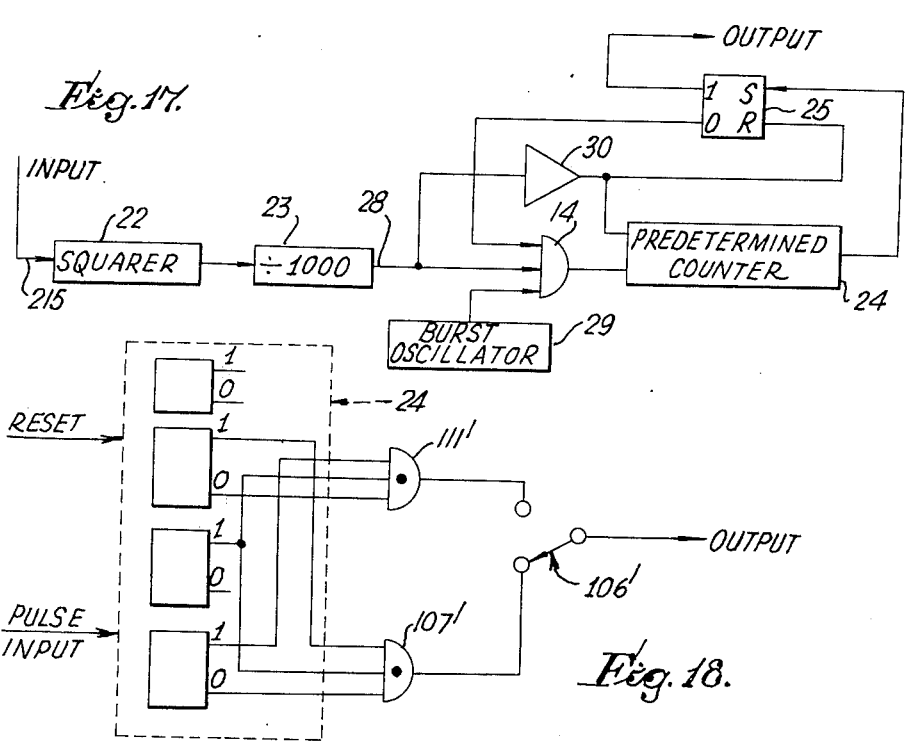
Fig. 17.
Fig. 18.

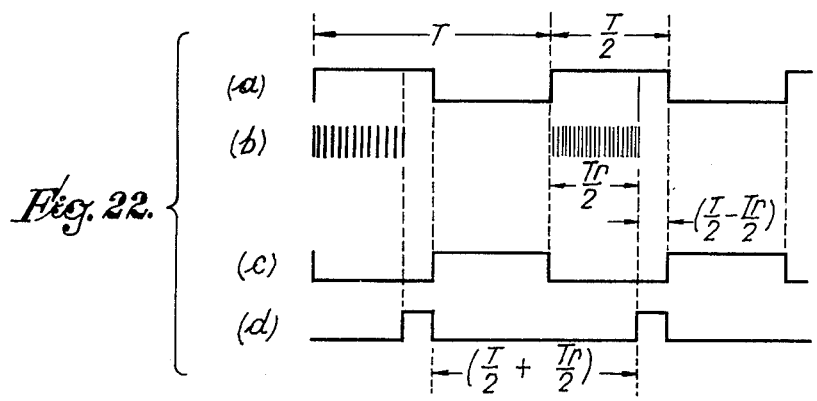
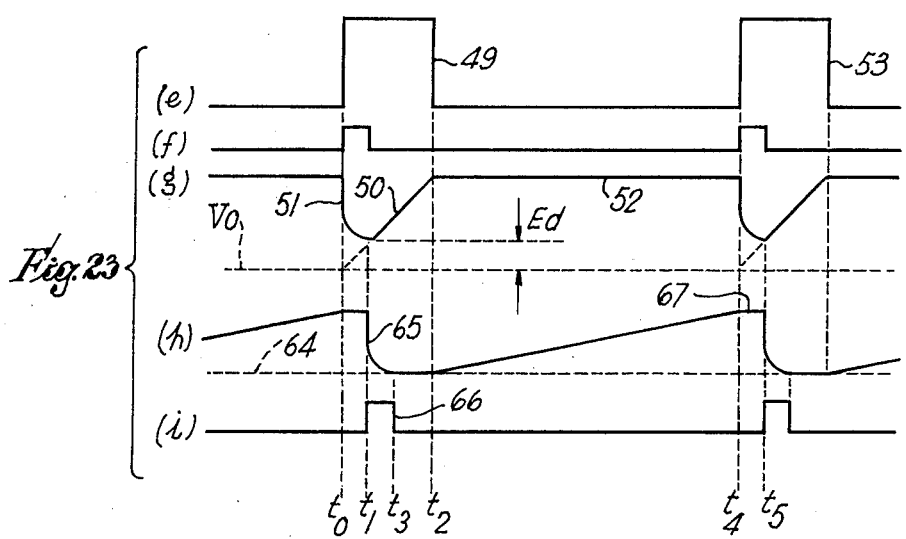

FLUID SENSING SYSTEMS

BACKGROUND OF THE INVENTION

This is a division of copending application Ser. No. 187,948, filed Oct. 12, 1971, for FLUID SENSING SYSTEMS. The benefit of the filing date of said copending application is, therefore, hereby claimed for this application.

This invention relates to devices for determining the character of fluids, and more particularly, to apparatus for producing signals in accordance with the density and/or volume of fluid.

In the past, it has been very difficult to measure the percent oil in an oil/water mixture flowing in a pipeline. For example, visual indications of total flow of both oil and water have been difficult to produce.

SUMMARY OF THE INVENTION

In accordance with the systems of the present invention, the above-described and other difficulties are overcome by providing a net oil computer including a gate generator.

It is a feature of the invention that the net oil computer has a densitometer that has utility in systems wholly different from that of the net oil computer, the densitometer incorporating a special feature of the invention including a self-start circuit which automatically shuts itself off.

An outstanding, wholly independent feature of the invention resides in the use of a magnetostrictive drive which has a certain input signal phase relationship for resonance at maximum efficiency.

The above-described and other advantages of the present invention will be better understood from the following detailed description when considered in connection with the accompanying drawings.

BRIEF DESCRIPTION OF THE DRAWINGS

In the drawings which are to be regarded as merely illustrative:

FIG. 6 is a perspective view of a densitometer probe constructed in accordance with the present invention;

FIG. 7 is a sectional view of the probe taken on the line 7—7 shown in FIG. 6;

FIG. 8 is a perspective view of a group of component parts of the probe shown in FIG. 6;

FIG. 9 is a transverse sectional view of the assembly taken on the line 9—9 shown in FIG. 8;

FIG. 10 is an enlarged longitudinal sectional view of a portion of the prove shown in FIG. 6;

FIG. 11 is a longitudinal sectional view of a portion of mounting means for an electrical connector otherwise substantially fixed relative to the probe taken on the line 11—11 shown in FIG. 7;

FIG. 15 is a schematic diagram of still another block shown in FIG. 12;

FIG. 16 is a detailed block diagram of one of the blocks shown in FIG. 12;

FIG. 17 is a block diagram of a pulse former circuit shown in FIG. 16;

FIG. 18 is a block diagram of a predetermined counter shown in FIG. 17;

FIGS. 22 and 23 are graphs of groups of waveforms characteristic of the operation of the invention.

DESCRIPTION OF THE PREFERRED EMBODIMENT

Figure 1:
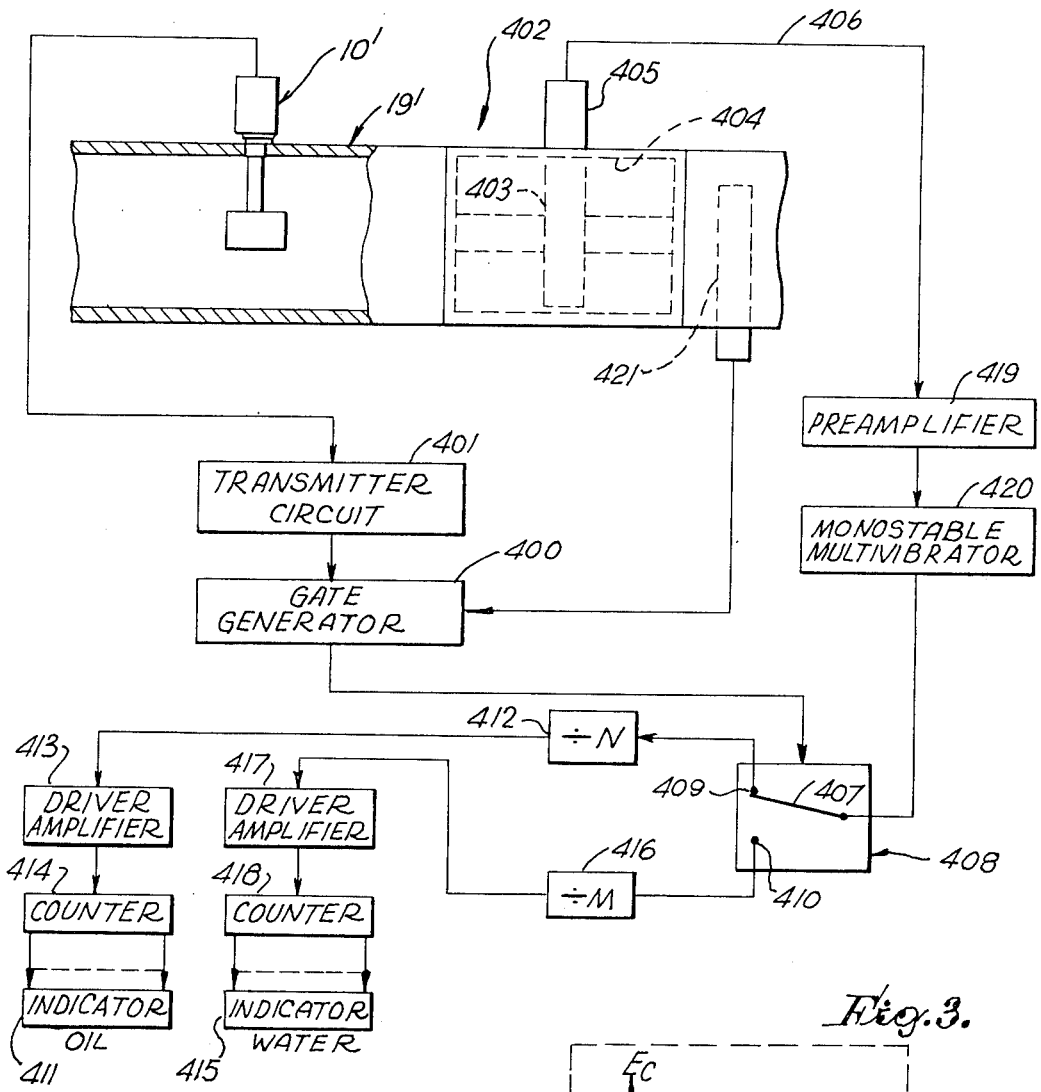
FIG. 1 is a diagrammatic view of the net oil computer.

The Net Oil Computer of FIG. 1

Figure 12:
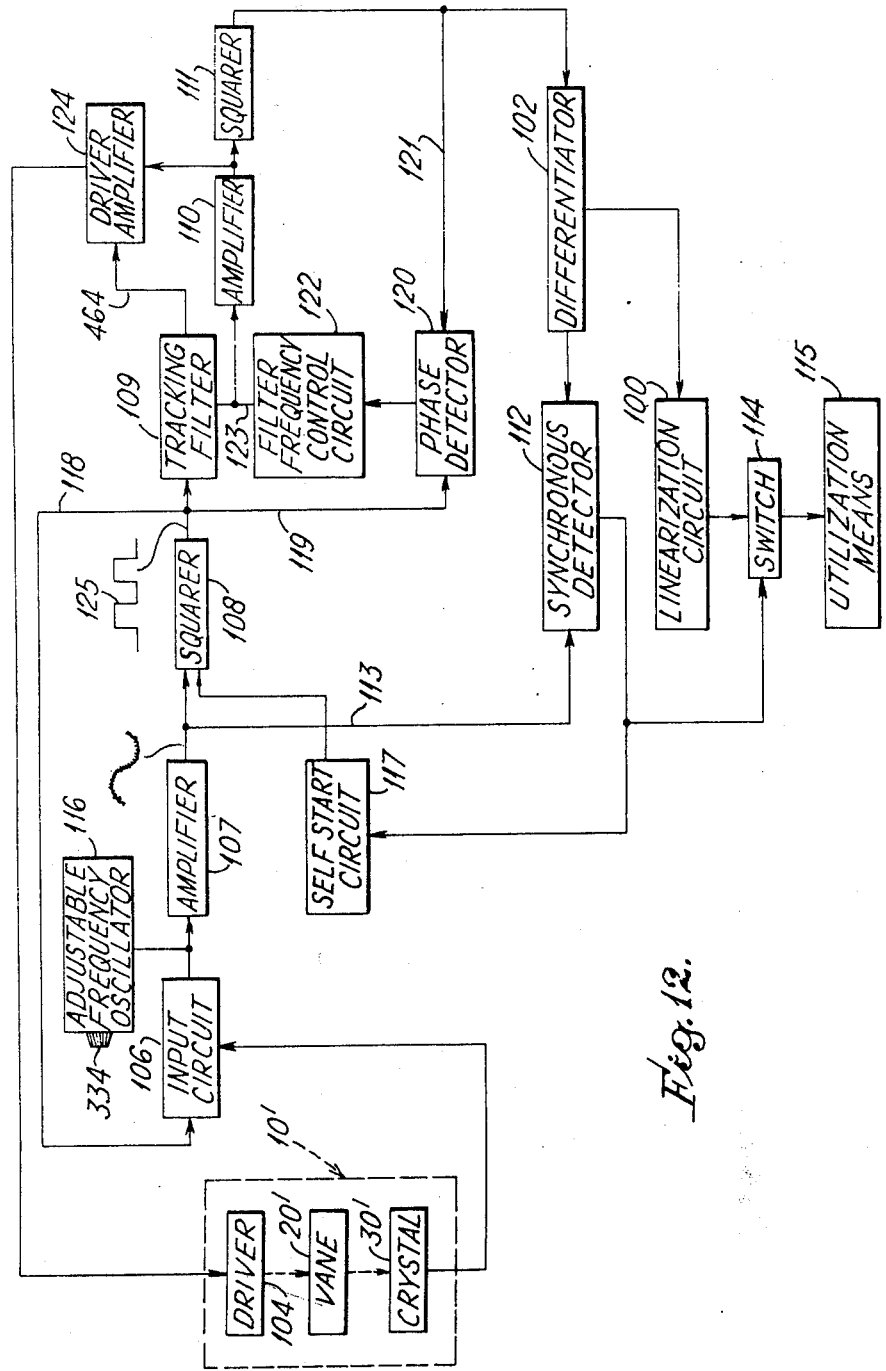
FIG. 12 is a block diagram of a densitometer constructed in accordance with the present invention.

A net oil computer constructed in accordance with the present invention is shown in FIG. 1. This computer has components mounted in a pipeline 19'. One component is a densitometer probe 10' having its output connected to a transmitter circuit 401. The probe 10' and the transmitter circuit 401 form a densitometer shown in FIG. 12. Probe 10' has also been shown in FIG. 12. A utilization means 115 which may be the net oil computer shown in FIG. 1, without probe 10' and transmitter circuit 401, is also shown in FIG. 12. Thus, transmitter circuit 401 includes all the structure shown in FIG. 12 with the exception of probe 10' and utilization means 115.

Circuit 401 produces an output current which is directly proportional to the density of the mixture of water and oil in pipeline 19'.

In FIG. 1, the net oil computer also includes a turbine flowmeter 402 which has a turbine bladed rotor 403 and a stator 404. Flowmeter 402 also has a magnetic pickup 405. Flowmeter 402 is entirely conventional and produces a pulse train on an output lead 406. The pulse repetition frequency (PRF) of the pulses on lead 406 is directly proportional to the volume flow rate within pipeline 19'. In other words, the flow rate is the rate of flow of both oil and water combined. The output of flowmeter 402 is impressed on the pole 407 of a switch 408. Switch 408 may be a relay, an electronic switch or otherwise. Relay 408 has contacts 409 and 410. Contact 409 is connected to an indicator 411 via a divider 412, a driver amplifier 413 and a counter 414. Contact 410 is connected to an indicator 415 through a divider 416, a driver amplifier 417 and a counter 418.

Flowmeter 402 is connected to switch pole 407 through a preamplifier 419 and a monostable multivibrator 420.

Switch 408 is operated by a gate generator 400 that receives input signals from transmitter circuit 401 and a temperature probe 421.

Dividers 412 and 416 may be employed to cause indicators 411 and 415 to read directly in barrels of oil and barrels of water, respectively.

If indicator 411 shows total oil flow and indicator 415 shows total water flow, if the output pulse of generator 400 is positive, as described hereinafter, when this pulse is received, pole 407 engages contact 409. That is, the engagement occurs during the width of the pulse. Conversely, during the time between pulses, pole 407 engages contact 410.

Figure 2:
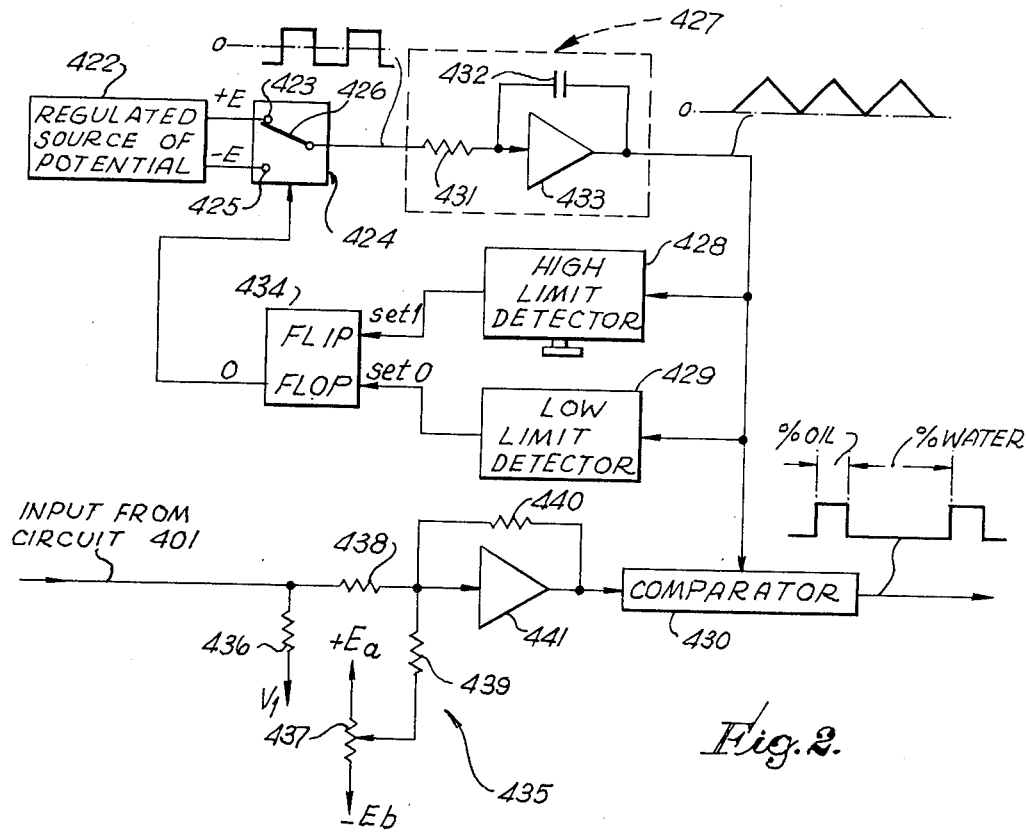
FIG. 2 is a diagrammatic view of a gate generator shown in FIG. 1.

Gate generator 400 is shown in FIG. 2 including a regulated source of potential 422 which places a voltage +E on a contact 423 of a switch 424. Source 422 also places a voltage −E on a contact 425. Switch 424 is a single-pole, double-throw switch having a pole 426. Switch 424 may be a relay, an electronic switch or otherwise. An integrator 427 is connected from the pole of switch 424 to a high limit detector 428, a low limit detector 429 and a comparator 430. The output of comparator 430 is impressed upon switch 408, shown in FIG. 1. Integrator 427 includes an input resistor 431, a feedback capacitor 432 and an amplifier 433. Detectors 428 and 429 are connected, respectively, to the set "1" and set "0" inputs of a flip-flop 434. The 0 output of flip-flop 434 operates switch 424.

High limit detector 428 causes the output of integrator 427 to decline after a predetermined high level is reached. Conversely, low limit detector 429 causes the output of integrator 427 to increase once a predetermined low level is reached. Thus, the output of the integrator 427 is a triangular wave, the peaks of which are the predetermined high limit and the valleys of which are the predetermined low limit. Thus, when the 0 output of flip-flop 434 is high, switch pole 426 is in engagement with contact 423. Conversely, when the 0 output of flip-flop 434 is low, pole 426 is in engagement with contact 425.

Figure 3:
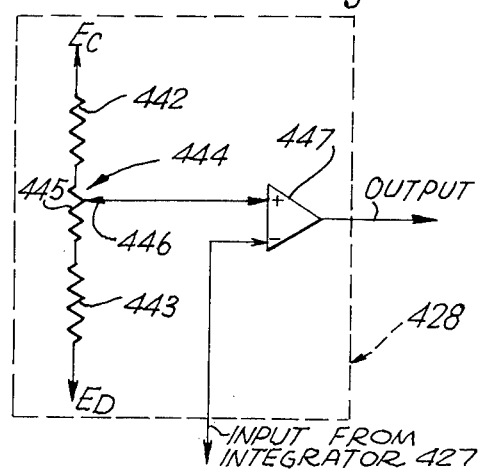
FIG. 3 is a schematic diagram of a high limit detector shown in FIG. 2.

As will be explained, the output of circuit 401 in FIG. 1 is a current analog of density. A circuit 435, shown in FIG. 2, converts the current analog to a voltage analog. Circuit 435 includes a resistor 436, a potentiometer 437, a resistor 438, a resistor 439, a resistor 440 and an amplifier 441. The output of circuit 435 is impressed upon comparator 430. High limit detector 428 is shown in FIG. 3 including resistors 442 and 443 connected in series with potentiometer 444 having a winding 445 and a wiper 446. Potentiometer 442 is connected to a source of potential $E_c$. Resistor 443 is connected to a source of potential D. Wiper 446 is connected from the plus input of an amplifier 447. The minus input of amplifier 447 receives the output of integrator 427.

Figure 4:
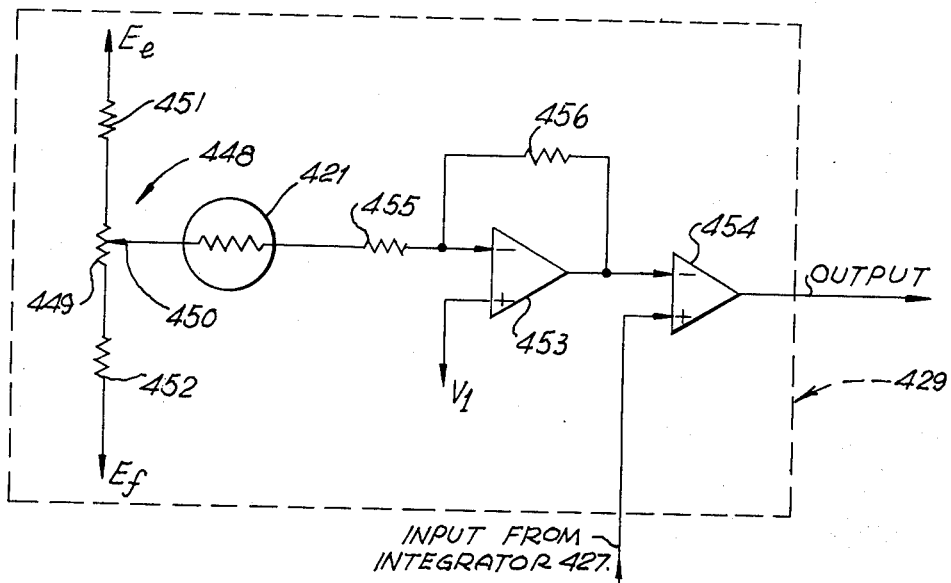
FIG. 4 is a schematic diagram of a low limit detector shown in FIG. 2.

As shown in FIG. 4, a somewhat similar arrangement includes a potentiometer 448 having a winding 449 and a wiper 450. The position of wipers 446 and 450 is determined by characteristics of the oil and water in pipeline 19'. That is, a sample is taken and put through a centrifuge. The specific gravity of the oil and water so separated is then found. The wiper locations on the potentiometers 444 and 448 are then set in proportion to the specific gravities measured. Various specific gravities may be encountered due to impurities, dissolved solids and otherwise. The specific gravity of the water in pipeline 19' might typically be 1.07. The oil in pipeline 19', which may or may not be crude oil, may have a typical specific gravity of 0.85. The high limit set by the location of wiper 446 thus is set in accordance with the specific gravity of the water. The location of wiper 450 is then set in accordance with the specific gravity of the oil.

In FIG. 4, low limit detector 429 also includes resistors 451 and 452 connected, respectively, from the ends of winding 449 in series therewith to sources of potential $E_e$ and $E_f$. Detector 429 also includes amplifiers 453 and 454. Probe 421 is simply a temperature sensitive resistor having a positive temperature coefficient of resistance. Probe 421 is thus connected to the minus input of amplifier 453 from wiper 450 through a resistor 455. Amplifier 453 has feedback resistor 456. The plus input of amplifier 453 is maintained at potential V1. The output of amplifier 453 is impressed upon the minus input of amplifier 454. Amplifier 454 receives a plus input from integrator 427. The output of detector 428 in FIG. 3 is thus impressed upon the set 1 input of flip-flop 434, and the output of detector 429 in FIG. 4 is impressed upon the set 0 input of flip-flop 434.

Figure 5:
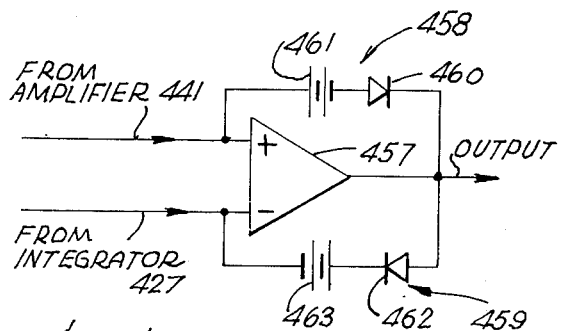
FIG. 5 is a schematic diagram of a comparator shown in FIG. 2.

Comparator 430, shown in FIGS. 2 and 5, produces an output pulse of a time width equal to the time that the triangular wave output of integrator 427 exceeds the magnitude of the voltage at the output of amplifier 441. Although it is unobvious and quite unexpected, the width of the output pulses of comparator 430 is directly proportional to the percent oil flowing in pipeline 19'. Further, the time between pulses is directly proportional to the present water flowing in pipeline 19'.

Probe 421 supplies a correction because the density of oil varies enough with temperature that a noticeable improvement in accuracy can be obtained by using a temperature correction.

Comparator 430 may be conventional or as shown in FIG. 5 including an amplifier 457 having a plus input connected from the output of amplifier 441 and a minus input connected from integrator 427. Amplifier 457 has two feedback paths 458 and 459. Path 458 includes a diode 460 and a source of potential 461. Path 459 includes a diode 462 and a source of potential 463.

Operation of the Net Oil Computer of FIG. 1

In the operation of the net oil computer of FIG. 1, flowmeter 402 continuously supplies pulses to pole 407 of switch 408 with a PRF directly proportional to the rate of volume flow. What switch 408 does is to divert a portion of these pulses to counter 414 and the remaining portion to counter 418. The percent diverted to counter 414 is directly proportional to the percent oil in pipeline 19'. The portion diverted to counter 418 is directly proportional to the percent water in pipeline 19'.

The manner in which switch 408 is operated to divert the appropriate percentages of pulses to the counters 414 and 418 is through the use of the densitometer including probe 10' and transmitter circuit 401, and gate generator 400. Gate generator 400 produces an output pulse, the width of which is directly proportional to the percent oil. Since this pulse is employed to operate switch 408, the corresponding percentages are produced.

The Probe 10' of FIG. 1

In FIG. 6, the probe 10' of the present invention is again shown having a shank 11', a housing 12' at its upper end, a tubular assembly 13' at its lower end, and an electrical connector assembly 14' at the upper end of housing 12' fixed thereto by bolts 15'. Annular fittings 16' and 17' extend around shank 11' for mounting probe 10' in a hollow cylindrical extension 18' of pipeline 19', as shown in FIG. 7.

As shown in FIGS. 6 and 7, a stainless steel vane 20' is mounted in assembly 13' in a position perpendicular to the axis of a hollow cylindrical magnetostrictive inner tube 21'. Vane 20', if desired, may be also mounted in a symmetrical position with respect to the axis of an outer sleeve 22' which houses it.

Vane 20' may be a rectangular plate having flat and parallel upper and lower surfaces as shown in FIG. 7, and may otherwise have mutually normal surfaces forming a right parallelopiped. Shank 11' not only includes inner tube 21', but an outer magnetic tube 23'. A drive coil or solenoid winding 24' wound on a nylon bobbin 25' is press fit onto the external surface of inner tube 21' and located in a space between the tubes 21' and 23' toward the lower end of shank 11'. Coil 24' is thus maintained in a substantially fixed position on inner tube 21', although the same is not necessarily critical to the operation of the device of the present invention.

Vane 20' is supported between two half cylinders 26' and 27' as shown in FIGS. 7 and 8. According to the invention, the longitudinal edges of vane 20' are pressed together between half cylinders 26' and 27' with a pressure of, for example, 20,000 pounds per square inch because the assembly shown in FIG. 8 is inserted in sleeve 22' with an interference fit, sleeve 22' being heated prior to the said insertion. A workable alternative is to electron beam weld vane 20' to half cylinders 26' and 27'. The welded assembly may then also be subjected to pressure by the said interference fit. However, the following description relates to the unwelded alternative.

Half cylinder 26' has four projections 28', and half cylinder 27' has four projections 29'. Projections 28' and 29' serve to prevent longitudinal movement of vane 20' between half cylinder 26' and half cylinder 27' although the same is not likely due to the clamping pressure on vane 20' between half cylinder 26' and half cylinder 27'.

Half cylinders 26' and 27', and vane 20' may be machined to have a flat or recess to receive a piezoelectric crystal 30'. Crystal 30' has electrical leads 31' and 32' which extend around half cylinders 26' and 27' in grooves 33' and 34', respectively, to a point where they enter the hollow interior of inner tube 21'. This entry is made at the lower end of inner tube 21', as shown in FIG. 7.

As shown in FIG. 8, projections 28' and 29' may have a slight separation at 35' to insure that the pressure contact of half cylinders 26' and 27' on vane 20' is quite high due to the said interference fit.

As shown in FIG. 7, a boss 36' is welded at 37' to sleeve 22' in a fluid tight manner. Although the device of the present invention need not always be fluid tight throughout, a glass-to-metal seal or other seal may be provided inside inner tube 21' for leads 31' and 32'. Before the said interference fit is provided, if desired, crystal 30', and those portions of leads 31' and 32' in grooves 33' and 34', respectively, may be potted with an epoxy. Further, after the interference fit has been effected, the entire unit when completely assembled may be treated further by applying a bonding agent around all of the structures inside sleeve 22'. Any conventional bonding process may be employed including, but not limited to, the application of a bonding agent sold under the tradename of "locktite".

As stated previously, boss 36' may be welded to sleeve 22' at 37' in a fluid tight manner. Further, outer tube 23' may be threaded onto boss 36' and welded thereto at 38' in a fluid tight manner. For all practical purposes, boss 36' may thus be considered an integral part of outer tube 23'. Boss 36', for example, is also made of a magnetic material. All of the "magnetic materials" referred to herein may be any magnetic material including, but not limited to, stainless steel. However, inner tube 21', although being magnetic, is also magnetostrictive. It is to be noted, however, that inner tube 21' is employed to produce vibration.

Inner tube 21' has an annular projection 39' with a shoulder 40'. Outer tube 23' has a lower bore 41' separated from a smaller upper counter bore 42' by an annular shoulder 43'. Shoulders 40' and 43' abut. From shoulder 40' to the lower end of inner tube 21', inner tube 21' is always in axial compression. That is, inner tube 21' is in compression when coil 24' is either energized or deenergized. Coil 24' is energized with a level shifted sine wave current which thus merely changes the degree of compression of inner tube 21'. The current always flows in one direction. The energizing voltage may typically be a level shifted sine wave having an average value of 0.1 volt and maximum excursions of +25.1 volts and −24.9 volts.

Projection 39' has a hole 44' through which the electrical leads of coil 24' can pass from the location of coil 24' upwardly between tubes 21' and 23'.

The manner in which probe 10' is mounted in pipeline 19' is better illustrated in FIG. 10. In FIG. 10, note will be taken that outer tube 23' has an outwardly extending radial projection 45' on each side of which rubber O-rings 46' and 47' are compressed by fittings 16' and 17'. Fitting 17' is threaded into extension 18' and sealed thereto by a conventional sealing component 48' shown in FIG. 7. In FIG. 10, note will be taken that fitting 16' is threaded inside fitting 17' at 49'. The amount O-rings 46' and 47' are compressed is, therefore, determined by the position of fitting 16'. That is, fitting 16' is turned, for example, by a wrench, until the desired O-ring compression is reached.

From the construction illustrated in FIG. 10, note will be taken that only O-rings 46' and 47' contact outer tube 23', and that, therefore, shank 11' is never touched by either fitting 16' or fitting 17'.

It is an advantage of the present invention that the construction of probe 10' is such that the leads from coil 24' are kept magnetically separate from the leads from crystal 30' in at least a portion of housing 12' as will be described. Housing 12' has a fitting 50' threaded onto outer tube 23'. A cylinder 51' is threaded to fitting 50'. A washer 52' is press fit and thereby fixed in fitting 50' and around inner tube 21'. Inner tube 21' has an upper end which may be fixed relative to or slidable in washer 52', as desired. However, preferably the external surface of inner tube 21' at its upper end fits contiguous to or in contact with the surface of washer 52' defining the hole therethrough. A shield 53' made of a magnetic material may be fixed around fitting 50' by one or two or more screws 54'. Outer tube 23' has a radial hole 55' therethrough through which the leads from coil 24' pass. Fitting 50' has a hole 56' therethrough in alignment with hole 55' through which the leads from coil 24' pass. From the outward radial extremity of hole 56', the coil leads indicated at 57' and 58' pass upwardly between cylinders 51' and shield 53' and are connected to pins 59' and 60' of the electrical connector 14'. Electrical connector 14' may be a conventional five pin connector.

As stated previously, the leads 31' and 32' from crystal 30' extend upwardly through the interior of inner tube 21'1 At the upper end of inner tube 21', as shown in FIG. 7, leads 31' and 32' are connected to the input of differential amplifier 61'. Leads 31' and 32' thus extend outwardly through the upper opening in inner tube 21'.

Differential amplifier 61' may be entirely conventional, and mounted on a conventional card, if desired. Amplifier 61' may be supported inside shield 53' by any conventional means, if desired, or simply supported by the strength of leads 31' and 32', and output leads 62' and 63' which are connected to pins 64' and 65' of connector 14', respectively. A lead 66' provides a ground connection from shield 53' to the fifth pin 67' of connector 14'.

The manner in which connector 14' is mounted on cylinder 51' is shown in FIG. 11. Only one bolt 15' is shown in FIG. 11 since all bolts 15' are similarly situated. In FIG. 11, bolt 15' is shown having a head 68', a washer 69' under head 68', an O-ring 70' under washer 69', and a shank 71' threaded into cylinder 51'. A second O-ring 72' extends around screw shank 71'. O-ring 70' fits between the lower surface of washer 69' and a counter sunk frusto-conical hole 73' in connector 14'. O-ring 72' fits between the upper surface of cylinder 51' and another counter sunk frusto-conical hole 74' in connector 14'. Holes 73' and 74' are connected by a bore 75'. From FIG. 11, it will be noted that all the structures shown therein may vibrate, but that the amount of vibration transmitted to connector 14' may be quite small. However, several features of the present invention are not limited to this construction.

The Densitometer of FIG. 12

In FIG. 12, probe 10' is shown including a magnetostrictive driver 104, a vane 20' and crystal 30'.

If desired, probe 10' may be identical to that disclosed in copending application Ser. No. 65,371 filed Aug. 20, 1970, for DENSITOMETER by C. E. Miller and G. L. Schlatter. The entire disclosure of said copending application is hereby incorporated by this reference hereto into the present application the same as though set forth in full herein hereat. The same is true of copending application Ser. No. 131,131 filed Apr. 5, 1971, for DENSITOMETER AND CALIBRATION METHOD AND APPARATUS THEREFOR by G. L. Schlatter. This application also contains some subject matter common to said copending application Ser. No. 65,371. The benefit of the filing date of said copending application Ser. No. 65,371 is, therefore, hereby claimed for this application.

The output crystal 30' is connected to an input circuit 106. An amplifier 107, a squarer 108, a tracking filter 109, an amplifier 110 and a squarer 111 are connected in succession from circuit 106 to a differentiator 102. Outputs of the differentiator 102 are connected to a synchronous detector 112 and to a linearization circuit 100, respectively. Synchronous detector 112 also receives an input over a lead 113 from the output of amplifier 107. The output of the synchronous detector 112 controls a switch 114 connected between linearization circuit 100 and utilization means 115. An adjustable frequency oscillator 116 is connected to the input of amplifier 107. A self-start circuit 117 is connected from synchronous detector 112 to squarer 108. The output of squarer 108 is impressed over a lead 118 on input circuit 106, and over a lead 119 on a phase detector 120. Phase detector 120 receives a second input on a lead 121 connected from the output of squarer 111. A filter frequency control circuit 122 is connected from the output of phase detector 120 to the control input of tracking filter 109. The output lead 123 of circuit 122 forms both the control input of filter 109 and the filtered output thereof, as will be described.

A driver amplifier 124 is connected from another output of filter 109 and from the output of amplifier 110 to driver 104.

As will be explained, input circuit 106 contains a differentiator which produces an output signal 90° out of phase with the output signal of crystal 30'. The output signal of tracking filter 109, introduced to amplifier 110, is also 90° out of phase with the input signal to tracking filter 109 from squarer 108. The two 90° phase shifts produced in input circuit 106 and tracking filter 109 can help or make it possible to connect the output of driver amplifier 124 to driver 104 in a manner to obtain resonance. That is, vane 101 is vibrated at its natural resonant frequency by energizing coil 24' with a level shifted alternating voltage in phase with the output of crystal 30'. The current flowing in coil 24' may be a level shifted sine wave, but it always flows in one direction only.

As will be explained, lead 118 supplied an isolated source of potential to input circuit 106.

Oscillator 116 is employed in calibration, as will be explained.

Circuit 117 is employed to insure self-starting. Synchronous detector 112 causes switch 114 to clamp the output of circuit 100 to a constant value when resonance does not occur.

Utilization means 115 may take any of several desired forms. When switch 114 passes the output of circuit 100, this output is directly proportional to the density of the fluid in which the probe 10' is submerged. Utilization means 115 may thus be a voltmeter or ammeter calibrated in density, as desired. Alternatively, utilization means 115 may be a process controller, gate generator 400 or otherwise.

Tracking filter 109 and linearization circuit 100 may have multiple ranges, if desired. This means the resonant vibration of vane 20' may occur anywhere within two or more bands depending upon in what fluid vane 20' is submerged. If such is the case, it is desirable for self-start circuit 117 to produce an output signal of a frequency which changes throughout a band of interest. Switching may be employed to switch the range of the frequency sweep of the output signal of circuit 117, if desired. However, as disclosed hereinafter, the frequency of the alternating output signal of self-start circuit 117 may vary from the lowermost limit of the lowermost band of operation of tracking filter 109 to the uppermost limit of the uppermost band of tracking filter 109.

The densitometer of FIG. 12 is, at least in part, an electromechanical oscillator. The crystal 30' is the pickoff, the output of which is amplified and impressed upon driver 104. However, there is, at times, due to pipe noise and otherwise, difficulty in starting the said electromechanical oscillator. The self-start circuit 117 automatically starts vane 20' vibrating at its natural resonant frequency for the density of the fluid in which it is submerged.

Self-start circuit 117, as will be described, may include two oscillators. One of the oscillators oscillates at a lower frequency than the oscillation frequency of the other oscillator. The higher frequency is thus frequency modulated in sinusoidal, saw-tooth or any other similar periodic wave fashion. When resonance is reached, self-start circuit 117 is turned off by the output of synchronous detector 112.

Driver amplifier 124 receives an additional input over a lead 464 from tracking filter 109. The input on lead 464 adjusts the phase of the alternating component of the output signal of driver amplifier 124 and by a simple resistor connection, unexpectedly makes the alternating component in phase with the output signal of crystal 30' over a band of frequencies of, for example, from 2.0 to 5.0 kilohertz.

According to an outstanding feature of the invention, the driver amplifier 124 impresses a signal on driver 104 having an alternating component which is in phase with the output signal of crystal 30'. From a review of FIGS. 6–11, it will be apparent that the substantial benefit obtained by this kind of drive is by no means obvious. The advantage is that resonance occurs at maximum efficiency. That is, when the output voltage of driver amplifier 124 has an alternating component in phase with the output of crystal 30', the amplitude of the output of crystal 30' is a maximum. This is true even though the alternating component of the current through coil 24' lags the alternating component of the input to driver 104 by about 70°, and this current phase does not change substantially throughout, for example, an entire frequency range of 2.0 to 5.0 kilohertz.

Driver amplifier 124 also has a voltage and current offset, to be described. This makes the output of crystal 30' of the same frequency as that of the output of driver amplifier 124. The current in coil 24 always flows in one direction. That is, it is more or less pulsating D.C. Typically, the output voltage of driver amplifier 125 is a sine wave having a peak voltage of about 25 volts, but an average value of from, for example, about 0.1 to 0.2 volt.

Another feature of the invention to be described includes means for maintaining the average value of the current in coil 24' constant and independent of its impedance or resistance. Reliable operation is thus assured even at cryogenic temperatures. This overcomes the problem of the D.C. resistance of the coil 24 dropping considerably at cryogenic temperatures.

Notwithstanding the foregoing, it will be appreciated that the densitometer of FIG. 12 may be used with the net oil computer of FIG. 1 or without it. That is, the densitometer of FIG. 12 may be used in many applications and is not limited to the net oil computer application. Further, the densitometer of the presnet invention may be used in providing an analog voltage or current directly proportional to either gas or liquid density for any purpose, control, indication or otherwise.

OPERATION OF THE DENSITOMETER SHOWN IN FIG. 12

In the operation of the densitometer of FIG. 12, calibration is accomplished by adjustment of oscillator 116 as will be described. Operation is then started when power is supplied. Circuit 117 then supplies an alternating output signal to squarer 108 which varies in frequency over a range of the instrument. When resonance is found, synchronous detector 112 stops oscillator 117 and tracking filter 109 follows the resonant signal. The output of tracking filter 109 is impressed upon driver amplifier 124 through amplifier 110 to cause the said electromechanical oscillator to oscillate. Vane 20' will then vibrate in one of its modes of vibration at a frequency which is a known function of the density in which it is submerged. Linearization circuit 100 then produces an output voltage and/or current analog directly proportional to density. This is impressed through switch 114 on gate generator 400, shown in FIG. 1. Alternatively, the output of switch 114 may be connected to the other utilization means 115, or to both.

Switch 114 may provide a zero or other voltage or current to utilization means 115, if desired, during such times that resonance does not occur. On an indicator, it thus can be determined that the instrument is not properly indicating density. Synchronous detector 112 produces an output signal. This selfsame output signal may be employed to operate both switch 114 and to start and stop self-start circuit 117.

Figure 13:
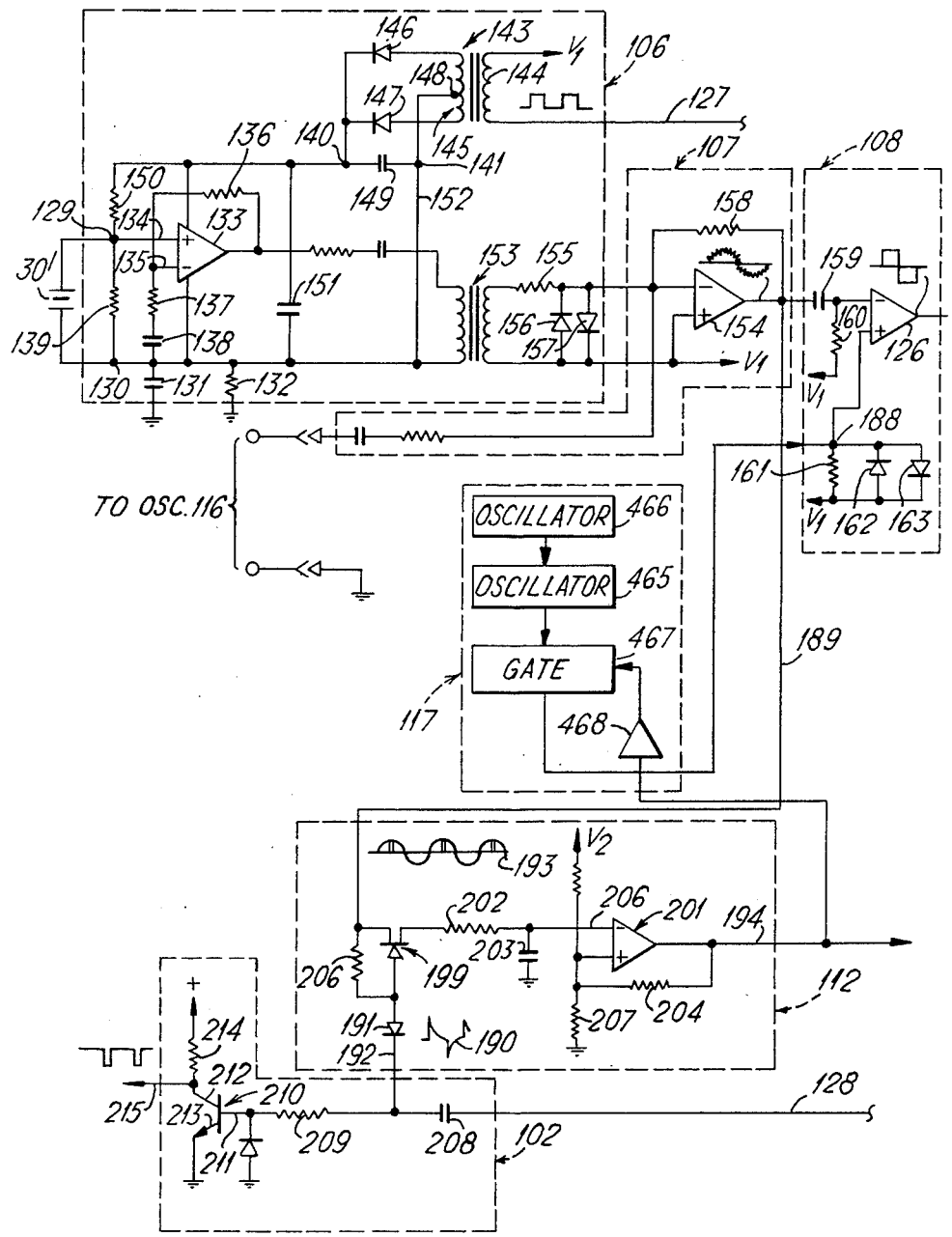
FIG. 13 is a schematic diagram of a portion of the blocks shown in FIG. 12.
Figure 14:
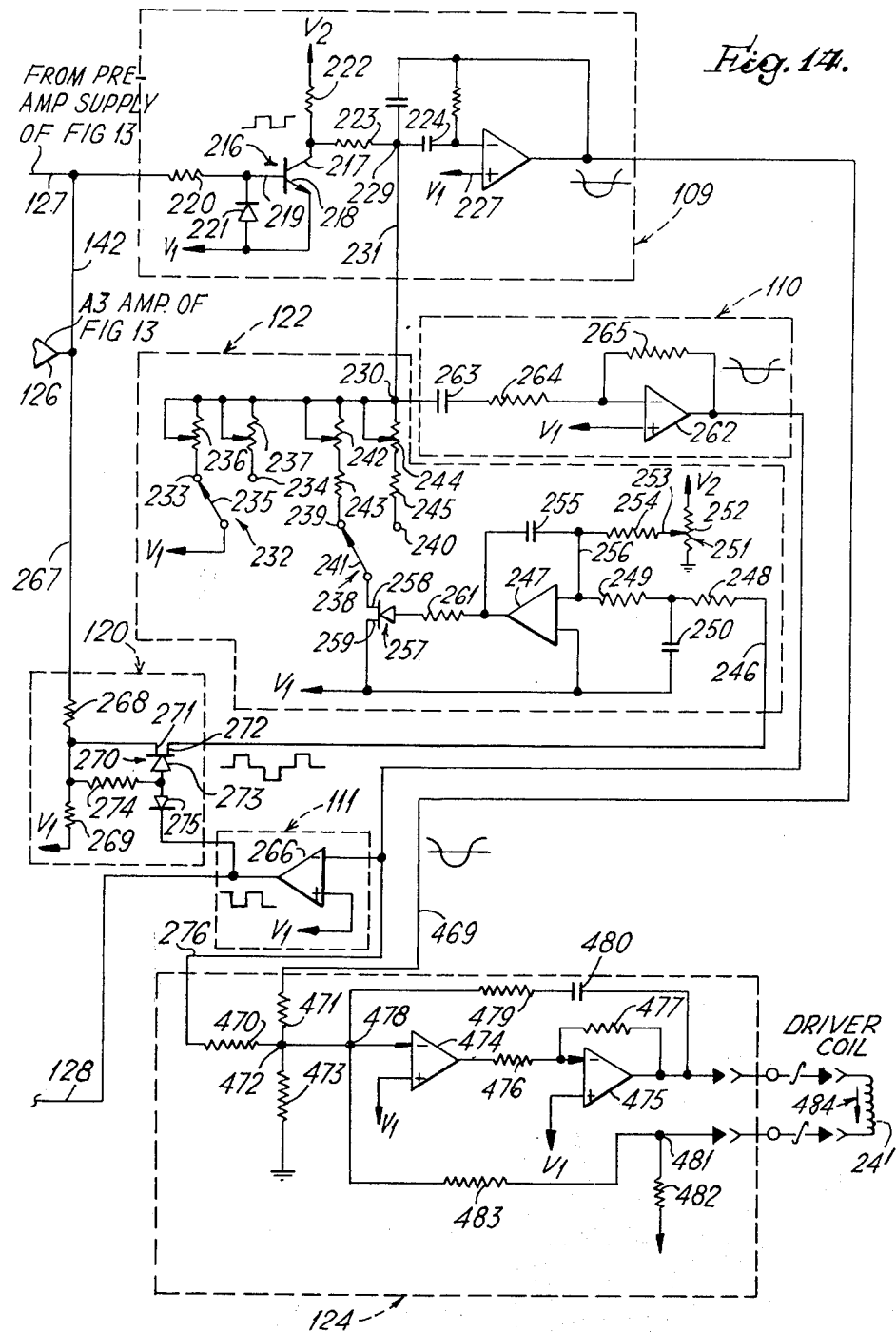
FIG. 14 is a schematic diagram of a portion of other blocks shown in FIG. 12.

If FIG. 13 is placed immediately to the left of FIG. 14, it will be noted that the leads fit together. For example amplifier 126 is duplicated in both FIGS. 13 and 14 for clarity. The same is true of lead 127 and lead 128.

In FIG. 13, input circuit 106 is shown connected from crystal 30'. Also shown are amplifier 107, squarer 108, circuit 117, synchronous detector 112 and differentiator 102.

In FIG. 14, tracking filter 109 is shown with circuit 122, amplifier 110, phase detector 120, squarer 111 and driver amplifier 124.

In FIG. 13, input circuit 106 is connected from crystal 30' at junctions 129 and 130. A capacitor 131 and a resistor 132 are connected from junction 130 to ground. A differential amplifier 133 has a plus input 134 and a minus input 135. A feedback resistor 136 is connected from the amplifier output to the minus input 135. A resistor 137 and a capacitor 138 are connected from the minus input 135 to junction 130. A resistor 139 is connected between junctions 129 and 130.

Input circuit 106 has power input terminals 140 and 141 connected from the output of amplifier 126 over a lead 142 and lead 127 to a transformer 143. Transformer 143 has a primary winding 144 connected from lead 127, and a secondary winding 145 with its ends connected to terminal 140 through diodes 146 and 147. Secondary 145 has a center tap 148 connected to terminal 141. A capacitor 149 is connected between terminals 140 and 141 to reduce the ripple. A resistor 150 is connected from junction 129 to terminal 140. A capacitor 151 is connected between terminal 140 and junction 130. A lead 152 connects terminal 140 to junction 130. The output of the circuit 106 is transformer coupled at 153 to an amplifier 154 in box 107 through a resistor 155 and diodes 156 and 157. Amplifier 154 has a feedback resistor 158. Squarer 108 is connected from the output of amplifier 154, and includes a coupling capacitor 159, a bias resistor 160, a bias resistor 161 and diodes 162 and 163.

Amplifier 107 has a coupling capacitor 164 and a series resistor 165 connected from oscillator 116.

In FIG. 13, self-start circuit 117 is again shown connected from output lead 194 of synchronous detector 112, and connected to junction 188 in squarer 108. Self-start circuit 117 includes an oscillator 465 connected from an oscillator 466 to a gate 467. The outputs of both oscillators 465 and 466 are periodic. These outputs may be sine wave, saw-tooth or other periodic waves. The frequency of oscillator 466 is lower than that of oscillator 465. The frequency of oscillator 465 varies in accordance with the amplitude of the output signal of oscillator 466. The output of oscillator 465 is impressed upon squarer 108 through gate 467. Gate 467 is open or closed based upon whether the output signal of an inverter 468 is high or low. Inverter 468 is connected from the said output lead 194 of synchronous detector 112.

Synchronous detector 112 is connected over a lead 189 from the output of amplifier 154. Waveform 190 is applied to detector 112 through a diode 101 over a lead 192. This causes the signal indicated at 193 on lead 189 to be sampled. If there is peak detection, an output appears at a lead 194 which is connected to a transistor 195 through a resistor 196 and a diode 197, as shown in FIG. 15. If there is peak detection, transistor 195 does not shunt the amplifier 198 to ground. It otherwise does.

In detector 112 in FIG. 13, sampling is accomplished by a field effect transistor 199 across which a resistor 206 is connected.

The output of field effect transistor 199 is connected to an amplifier 201 through a resistor 202 and a shunt capacitor 203. Amplifier 201 has a feedback resistor 204. Amplifier 201 has a plus input lead 205, and a minus input lead 206. Plus input lead 205 is connected to ground through a resistor 207, and to potential V2 through a resistor 207'.

Differentiator 102 includes a capacitor 208 connected in series with lead 128, a resistor 209 and a transistor 210. Transistor 210 has a base 211, a collector 212 and an emitter 213. Base 211 is connected from resistor 209. Emitter 213 is grounded. Collector 212 is connected to a positive source of potential through a resistor 214. A lead 215 is connected from collector 212 to linearization circuit 100. That is, lead 215 is the same as that shown in FIGS. 16 and 17.

As will be explained, filter 109 may be controlled to operate within two band limits.

Throughout the drawings, V2 may be 24 volts, and V1 may be 12 volts. However, theory of operation may be better understood by assuming V2, V1 and ground as shown in the drawings to be +12 volts, ground and −12 volts, respectively.

In FIG. 14, filter 109 includes a transistor 216 having a collector 217, an emitter 218 and a base 219. A resistor 220 is connected from lead 127 to base 219. A diode 221 is connected from base 219 to emitter 218. Emitter 218 is maintained at potential V1. A resistor 222 is connected from collector 217 to potential V2. A resistor 223 and a capacitor 224 are connected from collector 217 to the minus input 225 of an amplifier 226. The plus input 227 of amplifier 226 is connected to potential V1. A feedback resistor 228 is connected across amplifier 226. Filter 109 has a junction 229 which is connected to junction 230 in circuit 122 by a lead 231. A single-pole, double-throw switch 232 has contacts 233 and 234 and a pole 235. Potentiometers 236 and 237 are connected from junction 230 to contacts 233 and 234, respectively. A single-pole, double-throw switch 238 has contacts 239 and 240 and a pole 241. A potentiometer 242 and a resistor 243 are connected from junction 230 to contact 239. A potentiometer 244 and a resistor 245 are connected from junction 230 to contact 240. The pole 235 is connected to potential V1. The input to circuit 122 is provided by phase detector 120 on a lead 246 to an amplifier 247 through resistors 248 and 249. A capacitor 250 is connected from the junction of resistors 248 and 249 to potential V1. A potentiometer 251 having a winding 252 and a wiper 253 is connected from potential V2 to ground. A resistor 254 and a capacitor 255 are connected from wiper 253 to the output of amplifier 247. Resistors 249 and 254 are connected together by a lead 256. Circuit 122 has a field effect transistor 257 including a drain 258, a source 259 and a gate 260. A resistor 261 is connected from the output of amplifier 247 to gate 260. Source 259 is connected to potential V1. Drain 258 is connected to pole 241.

In amplifier 110, an amplifier 262 is connected from junction 230 through a capacitor 263 and a resistor 264. Amplifier 262 has a feedback resistor 265.

Squarer 111 includes simply an amplifier 266 driven to saturation. The output of amplifier 126 is impressed upon phase detector 120 on a lead 267 connected to resistors 268 and 269, resistor 269 being connected to potential V1. Phase detector 120 has a field effect transistor 270 with a drain 271, a source 272 and a gate 273. Drain 271 is connected from resistor 268. A resistor 274 connects resistor 268 to gate 273. A diode 275 is connected from the output of amplifier 266 to gate 273. Source 272 is connected to lead 246.

Driver amplifier 124 is shown in FIG. 14. It is connected from amplifier 110 over a lead 276. It is also connected from amplifier 226 in tracking filter 109 over a lead 469. The output of driver amplifier 124 is connected across coil 24'.

As shown in FIG. 14, driver amplifier 124 includes resistors 470 and 471 connected respectively from leads 276 and 469 to junction 472. A resistor 473 is connected from junction 472 to ground. Driver amplifier 124 also includes differential amplifiers 474 and 475. The minus input to amplifier 474 is connected from junction 472. The plus input to amplifier 474 is connected from potential V1. The output of amplifier 474 is connected to the minus input of amplifier 475 through a resistor 476. The plus input to amplifier 475 is connected to potential V1. A resistor 477 is connected from the minus input of amplifier 475 to the output thereof. Junction 472 is connected to the minus input of amplifier 474 through a junction 478. A resistor 479 and a capacitor 480 are connected in that order from junction 478 to the output of amplifier 475. Coil 24' is connected between the output of amplifier 475 and a junction 481. A resistor 482 is connected from junction 481 to potential V1. A resistor 483 is connected between junctions 478 and 481.

The driver amplifier 124, shown in FIG. 14, has several outstanding advantages. In the first place, it supplies a voltage to coil 24' which has an alternating component in phase with the output of crystal 30'. Moreover, the output voltage of driver amplifier 124 has an average value which is not zero. Even though it may be only 0.1 volt or 0.2 volt, this offset voltage completely prevents a current reversal in coil 24'. For example, if current flows in coil 24' in the direction indicated by arrow 484, current will never flow in a direction opposite the direction of arrow 484. This is generally true. Only a small level shift in the A.C. component of the coil voltage is necessary because the D.C. resistance of coil 24' is substantially less than the A.C. impedance thereof. For example, the D.C. resistance of coil 24' may be 14 ohms. The resistance of resistor 482 may be, for example, 1 ohm. The capacitance of capacitor 480 may be relatively large, e.g. 0.1 microfarad.

The additional input on lead 469 effectively shifts the phase of the signal on lead 276. Note will be taken that the signals on leads 276 and 469 will generally be sine waves. Thus, when sine waves of different phases are added together, the resulting wave is a sine wave whose phase is different from the phases of both of the waves which have been added together. The driver amplifier 124 effectively adds the waves on leads 276 and 469 together. The phase shift produced by the addition of the wave on lead 469 is desirable to compensate for the effective or ineffective operation of circuit elements or phase shifts therethrough. It is unexpected and an outstanding advantage of the present invention that the simple addition of waves, as aforesaid, makes the input voltage to coil 24' in phase with the output signal of crystal 30' over a band of frequencies of, for example, 2.0 to 5.0 kilohertz.

As stated previously, driver amplifier 124 impresses an alternating voltage on coil 24', the average value of which is not zero, but is only a small fraction of the peak voltage. However, the average value of the current through coil 24' is preferably equal to or somewhat larger than the amplitude of the alternating component of the coil current. The current is kept flowing in one direction only by the single resistor 483 with the resistor 482 acting to produce a voltage thereacross directly proportional to the current flowing in coil 24'. Typically, this offset voltage is between about 0.1 volt and 0.2 volt. The feedback connection of resistor 483 with resistor 482 keeps the current in the coil 24' constant at a value of, for example, 100 to 150 milliamperes. Typically, coil 24' has a D.C. resistance of from 10 to 15 ohms. Resistor 479 and capacitor 480 form a feedback circuit which holds the alternating component of the voltage across coil 24' constant at, e.g. 25 volts peak.

In FIG. 16, linearization circuit 100 of FIG. 12 is shown including a pulse former circuit 13, a first integrator 15, a second integrator 16 and a sample and hold circuit 10 connected in succession.

Figure 19:
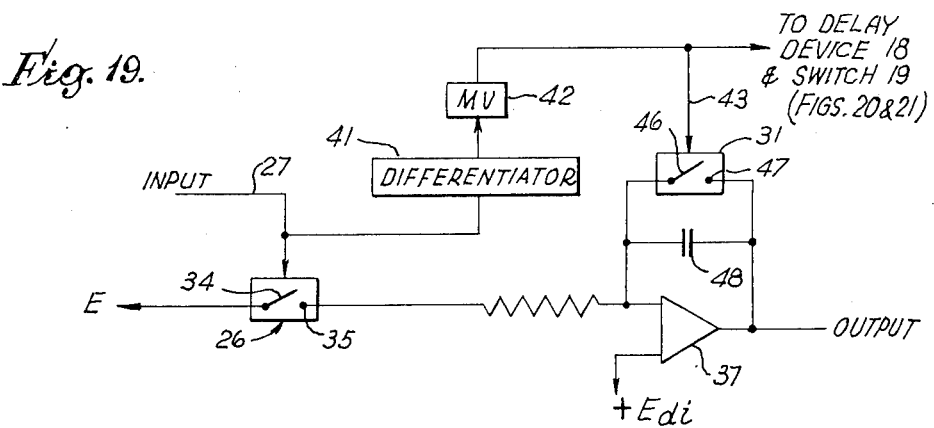
FIGS. 19 and 20 are schematic diagrams of integrators shown in FIG. 16.

As shown in FIG. 17, pulse former circuit 13 includes a squarer 22, a frequency divider 23, an AND gate 14, a predetermined counter 24 and a flip-flop 25, all of which are connected from differentiator 102 in FIG. 12 to a switch 26 in FIG. 19. The 1 output of flip-flop 25 is connected to an input lead 27 of switch 26. All the switches 26, 31, 32, 33 and 19, shown in FIGS. 19, 20 and 21, may be electromechanical or electrical, but preferably are electronic switches including, but not limited to, transistor switches. Thus, for example, the signal on input lead 27 of switch 26 closes switch 26 when the 1 output of flip-flop 25 is high.

A burst oscillator 29, shown in FIG. 17, is connected to a second input of gate 14. The 0 output of flip-flop 25 is connected to a third input of gate 14. The output of gate 14 is connected to the input of counter 24 in FIG. 17. An inverter 30 is connected from lead 28 to the reset input of flip-flop 25. The output of inverter 30 is also connected to the reset input of counter 24.

The operation of the pulse former circuit 13 of FIG. 17 may, perhaps, be best understood from the waveforms shown in FIG. 22. Pulse former circuit 13 converts waveform (a) to waveform (d). The output of divider 23 is indicated by waveform (a). The output of gate 14 is indicated by waveform (b). Gate 14 passes a burst of pulses from oscillator 29 to counter 24 over a period which may be called ($T_r/2$). The high output of divider 23 keeps gate 14 open. Initially, flip-flop 25 is in the 0 state and thus does not inhibit gate 14. Counter 24 then counts up the pulses in a burst and stops counting a period of time ($T_r2$) after the leading edge of each output pulse of divider 23. Counter 24 may be adjustable as to its predetermined count, if desired. Burst oscillator 29 produces pulses at a highly stable, constant high frequency.

Once the burst of pulses has been counted, counter 24 sets flip-flop 25 to the 1 state. The 0 output of flip-flop 25 then goes low and inhibits gate 14. No further pulses are then introduced to counter 24 until the leading edge of the next output pulse from divider 23. The output of inverter 30 is shown in waveform (c). When waveform (a) goes low, waveform (c) goes high, and both counter 24 and flip-flop 25 are reset. The 1 output of flip-flop 25 is thus illustrated in waveform (d).

Figure 20:
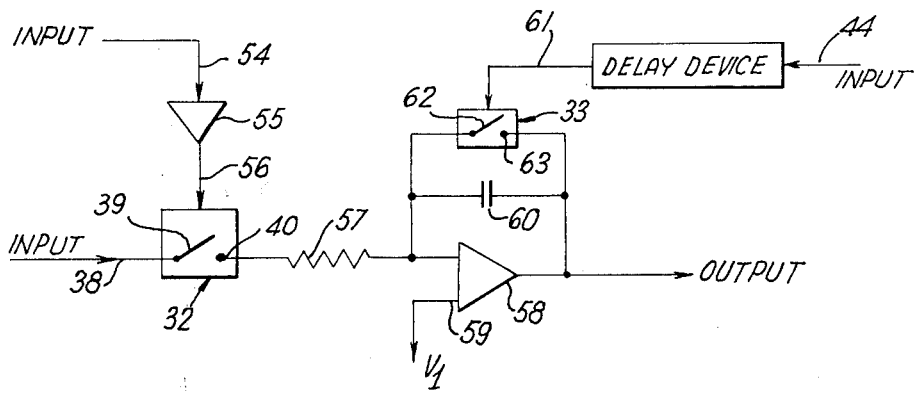
Figure 21:
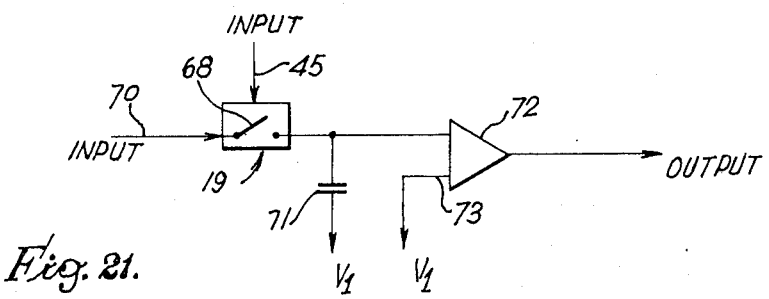
FIG. 21 is a schematic diagram of a sample and hold circuit shown in FIG. 16.

As will be evident from the following description, the vertical input leads to switches 26, 31, 32, 33 and 19, shown in FIGS. 19, 20 and 21, represent the actuating input leads. As described previously, the actuating input lead carries a voltage which, when high, causes the switch to close. Switch 26 has an arm 34 and a contact 35. A constant voltage, $E_o$, is connected to arm 34. A resistor 36 is connected between contact 35 and one input of a differential amplifier 37. The other input of differential amplifier 37 is connected to a constant voltage, $+E_{di}$. The input to switch 26 on lead 27 is connected from the 1 output of flip-flop 25, shown in FIG. 17, as stated previously. The output of amplifier 37, in FIG. 19, is connected to an input lead 38 connected to an arm 39 of the switch 32, switch 32 having a contact 40.

The counter 24, as shown in FIG. 18, may have either one of two predetermined counts determined by the position of single-pole, double-throw switch 106'. Two AND gates 107' and 111' are provided for two different corresponding counts.

In FIG. 19, first integrator 15 is shown including a differentiator 41 connected from lead 27 to a monostable multivibrator 42. The output of multivibrator 42 is connected to the actuating lead 43 of switch 31. The output of multivibrator 42 is also connected to an input lead 44 of a delay device 18 shown in FIG. 20, and to an actuating input lead 45 of switch 19, shown in FIG. 21.

In FIG. 19, switch 31 has an arm 46 and a contact 47. A capacitor 48 is connected from the output of amplifier 37 to the one input thereof to which resistor 36 is connected. Arm 46 is connected to the said one input of amplifier 37, and contact 47 is connected to the output thereof.

In the operation of the first integrator 15, shown in FIG. 19, the input to switch 26 on lead 27 closes switch 26 each time and a length of time that flip-flop 25 is in the 1 state. That is, switch 26 is closed during the widths of the pulses indicated in waveform (d). The integrator of FIG. 19, therefore, integrates during at least a portion of this time. However, due to the fact that integration is performed not only during the pulses of waveform (d), but also during the time between those pulses, one of the first and second integrators 15 and 16 of FIGS. 19 and 20, respectively, must be reset during its own integration interval. It is during this interval of the first integrator that such resetting takes place.

Differentiator 41 produces an output pulse at the leading edge of each of the pulses in waveform (d). Multivibrator 42 then produces an output pulse having a leading edge coinciding with the leading edge of each of the pulses of waveform (d) and having a trailing edge occurring before the trailing edges of the pulses of waveform (d). The output of multivibrator 42 is indicated by waveform (f) in FIG. 23. Waveform (e) is the same as waveform (d) although the scale thereof has been changed for clarity.

Receipt by switch 31 of the output of multivibrator 42 causes the capacitor 48 to discharge. Capacitor 48 is thus shunted through switch 31.

If capacitor 48 were completely discharged, at a time, $t_1$, shown in FIG. 11, the integrator would integrate from the zero line, $V_o$, starting at time, $t_1$. Since it is the object of the integrator of FIG. 19 to produce a maximum output at a time, $t_2$, which is directly proportional to the time width of pulse 49, shown in FIG. 19, an error would be introduced because the time $(t_1-t_0)$ would be omitted.

In accordance with the device of the present invention, this error is eliminated by preventing the output of amplifier 37 from falling below a predetermined constant voltage, $E_d$. This is done by supplying a suitable bias to amplifier 37, i.e. $E_{di}$. This provides the bias sufficient to maintain $E_d = St_r$, where S is the slope of line 50, and $t_r = t_1 - t_0$. Note that the line 50 thus extendds precisely through the point $t_o$, $V_o$ and makes the integration accurate for the entire width of pulse 49.

In accordance with the foregoing, as shown in FIG. 23, the output of amplifier 37 drops along the line 51, integrates along the line 50 and remains constant at 52 over a period between the trailing edge of pulse 49 and the leading edge of pulse 53. The output of amplifier 37 remains constant during the interval along the line 52 because during this period switch 26 is opened.

In FIG. 20, second integrator 16 is shown including an input lead 54 connected from the 1 output of flip-flop 25. An inverter 55 is connected from lead 54 to the actuating input lead 56 of switch 32. As stated previously, input lead 38 is connected from the output of amplifier 37. A resistor 57 is connected from switch contact 40 to one input of an amplifier 58. The other input is maintained at potential V1 at 59. As before, a capacitor 60 is connected from the output to the input of amplifier 58 which is connected to resistor 57. A delay device 18 is connected from an input lead 44 to an actuating input lead 61 of switch 33. Switch 33 has a pole 62, and a contact 63. Pole 62 is connected to the said one input of amplifier 58. Contact 63 is connected to the output thereof. The output of delay device 18 is indicated by waveform $(i)$ in FIG. 23. However, the pulse width and location of the output pulses of delay device 18 need not be exactly the same as that of waveform $(i)$.

Since reset occupies a portion of the widths of pulse 49 and 53 for the first integrator 15 of FIG. 19, no special precautions need be taken in connection with the second integrator 16 of FIG. 20. Thus, the output pulses of delay device 18 provide for reset. The outputs of amplifiers 37 and 58 are shown in waveforms $(g)$ and $(h)$, respectively. The output of amplifier 58 drops to zero volts at 64 on a line 65 produced by reset pulse 66. The output of amplifier 58 then stays at zero volts between $t_3$ and $t_2$ and integrates from $t_2$ to $t_4$. The inverted pulse input on lead 56 terminates the integration and the output of amplifier 58 remains constant at the line 67 between times $t_4$ and $t_5$.

First and second integrators 15 and 16, respectively, effectively integrate for periods from $t_1$ to $t_2$, and from $t_2$ to $t_4$, respectively. Thus, switch 26 s closed for the period time $t_0$ to $t_2$, and switch 32 is closed from $t_2$ to $t_4$.

First integrator 15, shown in FIG. 19, integrates at a rate directly proportional to the constant voltage, $E_o$. Thus, second integrator 16, shown in FIG. 19, integrates at a rate directly proportional to the voltage upon input lead 38, this voltage being the output voltage of amplifier 37 in FIG. 19. The voltage on input lead 38 is integrated between $t_2$ and $t_4$ because switch 32 is closed during this time.

Sample and hold circuit 10 is shown in FIG. 21 including switch 19 having an arm 68 and a contact 69. An input lead 70 to switch 19 connected from the output of amplifier 58 is shown in FIG. 20. Switch 19 has an actuating input lead 45 connected from the output of multivibrator 42 shown in FIG. 19. The sample and hold circuit 10 of FIG. 21 thus samples the amplitude of waveform $(h)$ between $t_0$ and $t_1$, between $t_4$ and $t_5$, etc. Note that switch 19 is closed over the duration of the pulses of waveform $(f)$. The entire circuit 10 of FIG. 21 may be conventional. A capacitor 71 is connected from switch contact 69 to potential V1. An amplifier 72 has one input connected from switch contact 69 and another input which is connected to potential V1 over a lead 73.

The invention produces a D.C. voltage at the output of circuit 10 directly proportional to the difference between the density of the fluid in which the densitometer probe is immersed, and a known, constant density.

If f is the resonant frequency of the vane 20', period, T, can be defined as, $$T = 1/f \qquad (1)$$

The densitometer of the present invention very accurately reproduces the equation, $$d = AT^2 + B \qquad (2)$$

where,
  $d$ is density, and
  A and B are constants.
If $d_r$ is some known, fixed density for a period, $T_r$, then, $$d_r = AT_r^2 + B \qquad (3)$$

Subtracting equation (3) from equation (2), $$d - d_r = A(T^2 - T_r^2) \qquad (4)$$

Factoring and dividing by four, $$d - d_r = 4A \left(\frac{T}{2} - \frac{T_r}{2}\right)\left(\frac{T}{2} + \frac{T_r}{2}\right) \qquad (5)$$

In FIG. 22, the output of divider 23 is indicated at waveform $(a)$. Note that each pulse has a period, T, and that each pulse has a width (T/2). In effect, pulse former 13 subtracts a known, constant pulse width from the first portion of each of the pulses $(a)$. Call this portion $(T_r/2)$. The output pulses of gate 14 are shown at $(b)$. Waveform $(c)$ is $(a)$ inverted. Pulses $(d)$ appear at the output of pulse former 13.

Note that the period between the trailing edges of pulses $(d)$ is T. The period between the trailing edge of the first and the leading edge of the next is thus, $$T - \left(\frac{T}{2} - \frac{T_r}{2}\right) = \left(\frac{T}{2} + \frac{T_r}{2}\right) \qquad (6)$$

Integrators 15 and 16 thus perform the computation, $$\left(\frac{T}{2} - \frac{T_r}{2}\right)\left(\frac{T}{2} + \frac{T_r}{2}\right) \qquad (7)$$

which is directly proportional to $d - d_r$. By adding the known constant, $d_r$, it is possible to arrive at absolute density.

Use of $d_r$ makes possible a more accurate computation and signal transmission because only the difference $d - d_r$ is computed and transmitted; and not absolute density, $d$.

Note that, $$d = A (T^2 - T_r^2) + d_r \qquad (8)$$

where,
$$d_r = AT_r^2 + B \qquad (9)$$

Equation (8) gives the output of amplifier 72 in terms of a voltage driectly proportional to $d$.

The word "spaced" as used herein and in the claims is hereby defined to include, but not be limited to, pulse spacing from center to center.

The word "densitometer" is hereby defined for use herein and in the claims to include a device which may or may not have utilization means 115 as described herein.

The output of sample and hold circuit 10, shown in FIG. 21, is connected to lead 295 in switch 114, shown in FIG. 15. Lead 295 is connected to potential V1 by a potentiometer 296 and a resistor 297. Potentiometer 296 has a winding 298 and a wiper 299. Amplifier 198 has a minus input 300, and a plus input 301. Wiper 299 is connected to minus input 300 by a resistor 302. Plus input 301 is connected to potential V1. A resistor 303 and a potentiometer 304 are connected from potential V2 to ground. Potentiometer 304 has a winding 305 and a wiper 306. A resistor 307 is connected from wiper 306 to minus input 300. A transistor 308 has a collector 309, an emitter 310 and a base 311. A diode 312 is connected from the output of amplifier 198 to base 311. Collector 309 is connected to a positive source of potential. Emitter 310 is connected to an output junction 313. A resistor 314 is connected from junction 313 to the minus input 300 of the amplifier 198. An amplifier 315 has a minus input 316 and a plus input 317. Junction 313 is connected to minus input 316 by a resistor 318. Plus input 317 is connected to potential V1. A resistor 319 is connected from potential V2 to minus input 316. Transistors 320 and 321 are connected from the output of amplifier 315. Transistor 321 has a collector 325, an emitter 326 and a base 327. Base 324 is connected from the output of amplifier 315. Collector 322 is connected to an output junction 328. Emitter 323 is connected to base 327. Emitter 326 is connected to minu input 316 of amplifier 315. Collector 325 is connected to junction 328. A milliammeter 329, a diode 330 and a resistor 331 are connected in series with junction 328. The output of switch 114 on lead 332 is between 4 and 30 milliamperes when transistor 195 does not short circuit the output of amplifier 198 to ground. Otherwise, there is a constant current of zero or some other constant current between 0 and 4 milliamperes. A resistor 333 shunts milliammeter 329.

For calibration, oscillator 116 in FIG. 12 may be turned on and adjusted to two frequencies of known outputs. Span potentiometer 296 and zero potentiometer 304 may then be adjusted.

The switches of circuit 122 and the switch 106' shown in FIG. 18, may all be ganged, if desired.

From the foregoing, it will be appreciated that synchronous detector 112 provides a sensitive device to detect whether or not resonance exists. At the same time, it actuates switch 114 to produce a constant output signal on lead 332 and to turn on circuit 117 when resonance does not exist.

Note will be taken that portions of and all of the structure of the densitometer including probe 10' and transmitter circuit 401 is an invention which can be used wholly independent of the net oil computer of FIG. 1 although its use therewith is very valuable. This is especially true of circuit 117, shown in FIG. 12, and/or the combination thereof with the other structures illustrated in FIG. 12. The same is true of the desirable phase control and the alternating and level shift components of both the voltage and current in the output of driver amplifier 124 and the structure which produces the phase control and said level shifted alternating voltages and currents. The same is true of the constant levels of the said alternating components.

In accordance with the foregoing, there are several features of the invention which are useful independently of one another. The sue of any such one feature may thus be made by itself or in combination with any one or more or all of the other features without departing from the invention.

Both of the dividers 412 and 416, shown in FIG. 1, may be entirely conventional. They may be fixed or adjustable, if desired. Both dividers 412 and 416 may be omitted under some circumstances, if desired.

Counters 414 and 418 may be binary digital counters or decimal coded binary counters or otherwise. Counters 414 and 418 may be entirely conventional.

Indicators 411 and 415, in FIG. 1, may be direct reading binary or direct reading decimal indicators. Indicators 411 and 415 may be entirely conventional.

A portion of the output of amplifier 226 is added on lead 469 to the signal on lead 276 in driver amplifier 124 in FIG. 14, as stated previously. What portion this is depends upon the magnitude of the resistance of resistor 471.

Amplifier 475 may be a noninverting amplifier. Amplifier 474 may be an inverting amplifier. A single inverting amplifier may replace both amplifiers 475 and 474. The capacitance of capacitor 480 may be 0.1 microfarad. The magnitude of the resistance of resistor 479 determines the magnitude of the A.C. output voltage of amplifier 475. The magnitude of the resistance of resistor 483 determines the average current through coil 24'.

A capacitor is not needed in parallel with resistor 482 to average the current because the voltage drop across resistor 482 is very, very small in comparison to the A.C. component of the voltage input to amplifier 474. The resistor 482 supplies the offset input voltage to amplifier 474 through resistor 483. This offset which is impressed across coil 24' is about 0.1 volt to 0.2 volt which remains relatively constant. The alternating component of the voltage across coil 24' is about 25 volts peak.

Note will be taken that the output of switch 114 in FIG. 12 during resonance is directly proportional to the density of the fluid in which vane 20' is submerged. In this same case, the output of switch 114 is also directly proportional to the specific gravity of the same fluid, the difference between density and specific gravity only being due to the constant factor of the density of water. Thus, for use herein and in the claims, any form of the phrase "specific gravity" is hereby defined to include "density" and vice versa.

What is claimed is:

1. A fluid flow sensing system, said system comprising: a flowmeter having an output lead and a first device for producing a train of pulses thereon of a pulse repetition frequency directly proportional to the volume rate of flow of a fluid through said flowmeter; a densitometer having an output lead and a second device for producing a signal thereon directly proportional to the specific gravity of said fluid; a first switch connected from said flowmeter output, said first switch having a switch position control lead; a first digital pulse counter connected from said first switch; and a gate generator connected from said densitometer output lead to said first switch, said gate generator producing an output pulse having a time width which is a predetermined percent of the period thereof, said predetermined percent being the percent of one of at least two different parts of said fluid, said first switch having first and second positions, said gate generator being adapted to hold said first switch in said first position during the generation of each output pulse of said gate generator and to hold said first switch in said second position thereof at all other times during normal operation, said first switch connecting said flowmeter output lead to the input of said first counter when said first switch is in one of said first and second positions and to disconnect said flowmeter output lead from said first counter all the normal operating time that said first switch is in the other of said first and second positions.

2. The invention as defined in claim 1, including a temperature probe adapted to be positioned adjacent the fluid, said probe being connected to said gate generator to vary the width of the output pulse thereof as a function of the temperature of said probe.

3. The invention as defined in claim 2, wherein said probe at least includes a temperature sensitive resistor.

4. The invention as defined in claim 1, including a second counter connected from said first switch, said first switch being constructed to connect said flowmeter output to said first and second counters when said first switch is in said first and second positions thereof, respectively, said first switch being constructed to disconnect said flowmeter output from said first and second counters when said first switch is in said second and first positions thereof, respectively.

5. The invention as defined in claim 4, including an indicator connected from each of said counters to display the corresponding counts thereof, said indicators being calibrated in volume measure.

6. The invention as defined in claim 1, including an indicator connected from said first counter to display the count thereof.

7. A fluid flow sensing system, said system comprising: a flowmeter having an output lead and a first device for producing a train of pulses thereon of a pulse repetition frequency directly proportional to the volume rate of flow of a fluid through said flowmeter; a densitometer having an output lead and a second device for producing a signal thereon directly proportional to the specific gravity of said fluid; a first switch connected from said flowmeter output, said first switch having a switch position control lead; a first digital pulse counter connected from said first switch; and a gate generator connected from said densitometer output lead to said first switch, said gate generator producing an output pulse having a time width which is a predetermined percent of the period thereof, said predetermined percent being the percent of one of at least two different parts of said fluid, said first switch having first and second positions, said gate generator being adapted to hold said first switch in said first position during the generation of each output pulse of said gate generator and to hold said first switch in said second position thereof at all other times during normal operation, said first switch connecting said flowmeter output lead to the input of said first counter when said first switch is in one of said first and second positions and to disconnect said flowmeter output lead from said first counter all the normal operating time that said first switch is in the other of said first and second positions, said gate generator including a comparator having a first input lead connected from said densitometer output lead, said comparator having an output lead connected to the control lead of said first switch, a first source of potential having first and second output leads, said first source being adapted to produce a constant potential $+E$ on said first lead thereof and a constant potential $-E$ on said second lead thereof, an integrator, cycle means to sample the said potentials $+E$ and $-E$ alternately, said cycle means being connected from said first source leads to the input of said integrator to impress a rectangular wave thereon having a high level of $+E$ and a low level of $-E$, said cycle means including a second switch connected from said first source leads to said integrator input, said second switch having a switch position control lead, a flip-flop having a set 1 input, a set 0 input and a 0 input, said 0 output being connected to said second switch control lead, said switch being actuable by said flip-flop to connect said first source first lead to said integrator when the integrator output first falls below the low limit of said low limit detector and to connect said first source second lead to said integrator input when the integrator output first rises above the high limit of said high limit detector, said high limit detector being connected from said integrator output and being constructed to set said flip-flop to the 1 state when said integrator output first has a magnitude greater than said high limit, said low limit detector being connected from said integrator output and being constructed to set said flip-flop to the 0 state when said integrator output first has a magnitude less than said low limit, said comparator having a second input lead connected from said integrator output, said comparator producing an output pulse on said output lead of a pulse width which is the time that the output signal magnitude of said integrator exceeds the magnitude of the signal on said comparator first input lead.

8. The invention as defined in claim 7, wherein each of said detectors includes a differential amplifier having one input connected from said integrator, said high limit detector including first means to supply a first potential to the other input of the said high limit detector amplifier directly proportional to the specific gravity of the part of said fluid having the greatest specific gravity, said low limit detector including second means to supply a second potential to the other input of said low limit detector amplifier directly proportional to the specific gravity of the other part of said fluid.

9. The invention as defined in claim 8, wherein said second means includes a temperature sensitive resistor for mounting adjacent the fluid, a second source of potential, said resistor being connected between said second source and said low limit detector amplifier.

10. The invention as defined in claim 9, wherein said first and second means are manually adjustable to adjust the potentials applied thereby to the said other inputs of said differential amplifiers.

11. The invention as defined in claim 10, including a second counter connected from said first switch, said first switch being constructed to connect said flowmeter output to said first and second counters when said first switch is in said first and second positions thereof, respectively, said first switch being constructed to disconnect said flowmeter output from said first and second counters when said first switch is in said second and first positions thereof, respectively.

12. The invention as defined in claim 11, including an indicator connected from each of said counters to display the corresponding counts thereof, said indicators being calibrated in volume measure.

13. The invention as defined in claim 12, wherein said one part of the fluid is oil, the fluid only having two parts, the other part of the fluid being water.

* * * * *